United States Patent [19]
Doubek et al.

[11] Patent Number: 5,533,503
[45] Date of Patent: *Jul. 9, 1996

[54] NASAL DILATOR

[75] Inventors: William J. Doubek, Circle Pines; Daniel E. Cohen, Eden Prairie; Bruce C. Johnson, St. Paul, all of Minn.

[73] Assignee: Creative Integration & Design, Inc., St. Paul, Minn.

[*] Notice: The term of this patent shall not extend beyond the expiration date of Pat. No. 5,533,499.

[21] Appl. No.: 314,547

[22] Filed: Sep. 28, 1994

Related U.S. Application Data

[63] Continuation of Ser. No. 50,554, Apr. 20, 1993, abandoned, and Ser. No. 183,916, Jan. 19, 1994, abandoned, which is a continuation of Ser. No. 48,589, Apr. 16, 1993, abandoned, which is a continuation of Ser. No. 884,626, May 15, 1992, abandoned, which is a continuation of Ser. No. 712,508, Jun. 10, 1991, abandoned, said Ser. No. 50,554, Apr. 20, 1993, abandoned, is a continuation-in-part of Ser. No. 48,589, Apr. 16, 1993, abandoned.

[51] Int. Cl.$^6$ .............................. A61F 5/08; A61F 5/56; A61M 15/08; A62B 7/00
[52] U.S. Cl. .................. 128/200.24; 128/207.18; 128/848; 606/204.45; 602/902
[58] Field of Search ................. 128/200.24, 207.18, 128/848, 857, 858, 204.12, 912, DIG. 26; 602/12, 16, 17, 60, 74, 902, 5, 6, 14, 46, 47, 61; 606/191, 196, 199, 201, 204.15, 204.45

[56] References Cited

U.S. PATENT DOCUMENTS

| | | | |
|---|---|---|---|
| 850,978 | 4/1907 | Soares | 128/163 |
| 1,043,924 | 11/1912 | Gottlieb | 606/199 |
| 1,292,083 | 1/1919 | Sawyer | 606/199 |
| 1,950,839 | 3/1934 | Chirila | 606/199 |
| 2,001,862 | 5/1935 | Battey | 128/163 |
| 2,398,073 | 4/1946 | Bonde | 128/87 R |
| 2,509,157 | 5/1950 | Lind | 128/87 |
| 3,046,989 | 7/1962 | Hill | 128/207.18 |
| 3,426,751 | 2/1969 | Radewan | 128/76 C |
| 3,742,943 | 7/1973 | Malmin | 128/76 C |
| 3,835,848 | 9/1974 | Berner | 128/76 C |
| 3,935,859 | 2/1976 | Doyle | 128/89 |
| 4,153,051 | 5/1979 | Shippert | 128/89 |
| 4,213,452 | 7/1980 | Shippert | 128/89 |
| 4,274,402 | 6/1981 | Shippert | 128/89 |
| 4,340,040 | 7/1982 | Straith | 128/76 C |
| 4,402,314 | 9/1983 | Goode | 128/87 R |
| 4,414,977 | 11/1983 | Rezakhany | 128/342 |
| 4,534,342 | 8/1985 | Paxa | 182/163 |
| 4,674,133 | 6/1987 | Oschner | 2/206 |
| 4,823,789 | 4/1989 | Beinsang, III | 128/207.18 |
| 4,932,943 | 6/1990 | Nowak | 604/180 |
| 4,984,302 | 1/1991 | Lincoln | 2/206 |
| 4,995,114 | 2/1991 | Price, Jr. | 2/15 |
| 5,003,971 | 4/1991 | Buckley | 128/156 |
| 5,022,389 | 6/1991 | Brennan | 128/858 |
| 5,101,837 | 4/1992 | Perrin | 128/888 |

FOREIGN PATENT DOCUMENTS

| | | | |
|---|---|---|---|
| 437661 | 11/1926 | Germany | 128/76 C |
| 12987 | 6/1899 | United Kingdom | 128/76 C |
| WO92/22340 | 12/1992 | WIPO | 128/858 |

OTHER PUBLICATIONS

CoNco Article "Nasal Splint", p. 12, Oct. 10, 172.

*Primary Examiner*—Kimberly L. Asher
*Attorney, Agent, or Firm*—Kinney & Lange

[57] ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing. An end edge tip structure of the first and second end regions prevents inadvertent peeling of the truss member from the outer wall tissue, caused by the resiliency of the first and second resilient bands.

41 Claims, 4 Drawing Sheets

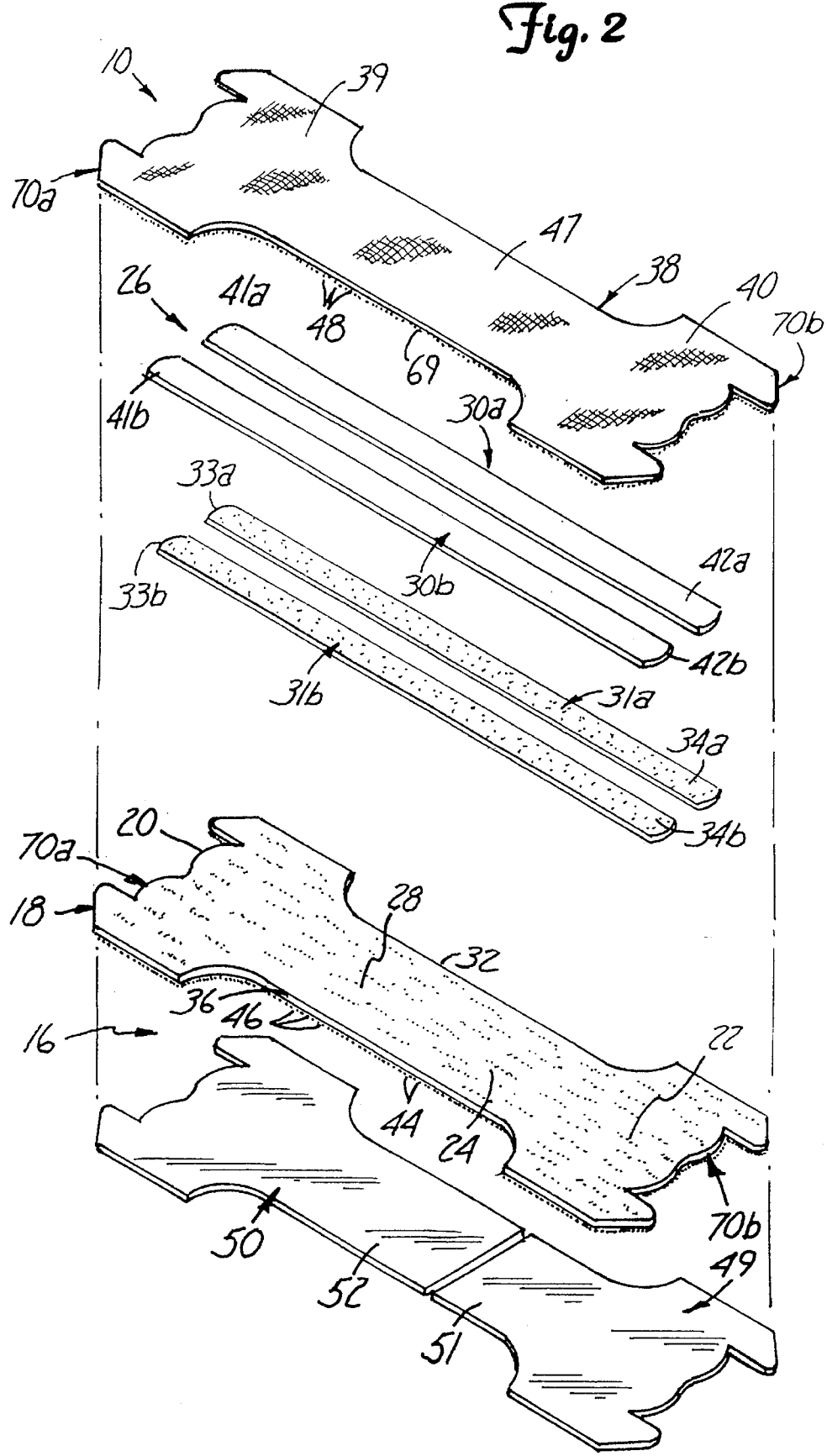

NASAL DILATOR

This is a continuation of the application having Ser. No. 08/050,554, filed on Apr. 20, 1993, now abandoned, which was the continuation-in-part of the application having Ser. No. 08/048,589, filed on Apr. 16, 1993, now abandoned, which was a continuation of the application having Ser. No. 07/884,626, filed on May 15, 1992, now abandoned, which was a continuation of the application having Ser. No. 07/712,508, filed on Jun. 10, 1991, now abandoned, and a continuation-in-part of application Ser. No. 08/183,916, filed Jan. 19, 1994, abandoned which is a continuation of application Ser. No. 08/048,589, filed Apr. 16, 1993, now abandoned, which is a continuation of application Ser. No. 07/884,626, filed May 15, 1991, now abandoned, which is a continuation of application Ser. No. 08/712,508, filed Jun. 10, 1991, now abandoned.

REFERENCE TO RELATED APPLICATIONS

Reference is made to U.S. patent application Ser. No. 07/884,626 filed on May 15, 1992 which is a Continuation of U.S. patent application Ser. No. 07/712,508 filed on Jun. 10, 1991 entitled NASAL DILATOR which is incorporated herein by reference thereto. Reference is further made to U.S. patent application Ser. No. 08/050,557 entitled NASAL DILATOR filed on even date herewith which is incorporated herein by reference thereto.

BACKGROUND OF THE INVENTION

This invention relates generally to the field of devices for the treatment of malformations. In particular, the present invention is a nasal dilator for preventing outer wall tissue of nasal passages of a nose from drawing in during breathing.

A portion of the human population has some malformation of the nasal passages which makes breathing difficult. Example of such malformations are a deviated septum and swelling due to allergic reactions. The lower portion of the nostril, immediately above the entrance to the nostril, is known as a vestibule. The vestibule tapers inwardly to a narrowed neck-like area called the nasal valve. Posterior to the nasal valve the nasal passages widen out again. Nasal obstructions commonly occur at the nasal valve in individuals who have swelling due to allergic reactions, a deviated septum or similar condition, to the point that the nasal valve may be substantially blocked. Commonly, the lateral wall (i.e., the outer wall tissue of the nasal passage) at the nasal valve is loose with the result that the outer wall tissue draws in during the process of inhalation to substantially or completely block the passage of air through the nasal passage.

Blockage of the nasal passages is obviously an inconvenience to persons who experience it. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances, sleep irregularities and/or snoring. In addition, a person with such a condition may wake often because he/she is not easily inhaling sufficient quantities of oxygen.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose are generally known. U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the nasal valve within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective since they are uncomfortable to wear. Because the nasal dilators must be inserted within the nasal passages they may cause irritation and itching. In addition, these nasal dilators must be custom-made to fit each nasal passage of an individual.

Another nasal dilator is disclosed in the U.S. Pat. No. 1,292,083 to Sawyer. This nasal dilator includes pads of adhesive material to which are attached metal loops. The pads are applied to the exterior surface of the nose above the nostrils. Once the pads are affixed, a dilating member is connected with each of the loops. The dilating member consists of a metal wire that provides a spring force which is directed outwardly or upwardly when hooked ends of the dilating member are engaged with the loops of the pads. A further nasal dilator is disclosed in the U.S. Pat. No. 1,950,839 to Chirila. This nasal dilator is similar to that of Sawyer but employs suction cups to secure a dilating member to the exterior surface of the nose.

These nasal dilators are not always effective in insuring free breathing because of their multiple element configurations that are designed to be assembled and then disassembled. Because these dilators are meant to be readily assembled and disassembled, the dilating members can easily become disengaged from the elements (i.e., the pads in Sawyer and the suction cups in Chirila) that secure the dilating members to the exterior of the nose. This unwanted disengagement of the elements could result in injury to the face or eyes of the wearer of the nasal dilators. Injury to the face and eyes is particularly likely during sleep, when the dilators are most likely worn since the wearer of the dilators, during any rolling over or the like, has little conscious control or awareness of the assembled or disassembled state of the dilators.

A still further nasal dilator is disclosed in the International Application Published Under The Patent Cooperation Treaty WO 92/22340 to Johnson. This nasal dilator comprises a truss member that includes a flexible strip of material having a first end region, a second end region and an intermediate segment. The first and second end regions are adapted to engage the outer wall tissue of first and second nasal passages of the nose and are secured thereto via an adhesive substance. The truss member further includes resilient bands that are secured to the strip of material by way of strips of double sided adhesive foam tape. The resiliency of the bands acts to stabilize the outer wall tissue and thereby prevents the outer wall tissue of the nasal passages from drawing in during breathing.

In the International Application, curved ends of the strip of material extend past angled ends of the resilient bands.

This configuration, helps to prevent the inadvertent peeling of the curved ends of the strip of material from the outer wall tissue of the nasal passages, caused by the spring biasing force exerted by the resilient bands. However, positioning the resilient bands on the strip of material, such that the bands are centered with respect to the curved ends of the strip of material, can be a tedious, cumbersome process that does not easily lend itself to an automated manufacturing process. Since to center the bands on the strip of material necessarily requires that the bands be precut prior to application to the strip of material, the bands may be secured to the strip of material in an uncentered, misaligned configuration. This inaccurate positioning of the bands may affect the overall effectiveness of the nasal dilator in providing free breathing to the nasal dilator wearer.

It is evident that there is a continuing need for improved nasal dilators for preventing outer wall tissue of nasal passages of a nose from drawing in during breathing. Specifically, there is a need for a nasal dilator that can provide effective relief without the need of inserting an object within the nasal passage. Moreover, there is a need for a nasal dilator that can be worn reliably at night when the nasal blockage problem is most acute and most uncomfortable. In addition, there is a need for a nasal dilator that can be reliably worn through extended therapeutic periods. The nasal dilator should be of efficient design and relatively uncomplicated to allow efficient manufacturing processes to be implemented to produce the nasal dilator. In addition, the nasal dilator should provide effective stabilization of the outer wall tissue of the nasal passages to provide effective relief from nasal blockage during inhalation. Moreover, this effective stabilization should be provided without undue discomfort to the wearer.

SUMMARY OF THE INVENTION

The present invention is a nasal dilator for preventing outer wall tissue of nasal passages of a nose from drawing in during breathing. The nasal dilator comprises a truss member having a first end region adapted to engage the outer wall tissue of a first nasal passage. A second end region of the truss member is configured to engage the outer wall tissue of a second nasal passage. The first and second end regions of the truss member are coupled to one another by an intermediate segment. The intermediate segment is configured to traverse a portion of the nose located between the first and second nasal passages. A resilient means extends along the truss member and has end portions that terminate at least at sections of end edges of the first and second end regions. The resilient means, when the truss member is in place, acts to stabilize the outer wall tissue and thereby prevents the outer wall tissue of the first and second nasal passages from drawing in during breathing.

The truss member includes a flexible strip of material that defines the first and second end regions and the intermediate segment of nasal dilator. The end edges of the first and second end regions employ a discontinuities of material (i.e., back cuts) that prevent inadvertent peeling of the strip of base material from the outer wall tissue of the first and second nasal passages caused by dilating forces imparted to the strip of base material by the resilient means.

A first resilient band of the resilient means is secured to a first side of the strip of material adjacent a first edge of the material. A second resilient band of the resilient means is spaced from the first resilient band is secured to the first side of the strip of material adjacent a second edge thereof. The first and second resilient bands are oriented generally parallel to one another and substantially parallel to the longitudinal extent of the strip of material. The resiliency of the first and second resilient bands prevents the outer wall tissue of the first and second nasal passages from drawing in during breathing.

The truss member further includes an adhesive substance located on a second side of the flexible strip of material. The adhesive substance acts to releasably secure the truss member to the outer wall tissue of the first and second nasal passages. First and second release liners cover the adhesive substance on the second side of the flexible strip of base material. The first and second release liners are readily removable from the strip of base material to expose the adhesive substance and permit the truss member to be secured to the outer wall tissue of the first and second nasal passages.

This nasal dilator is an efficient design that can be efficiently manufactured. The nasal dilator effectively prevents the outer wall tissue of the first and second nasal passages of the nose from drawing in during breathing. In addition, the nasal dilator provides effective relief of nasal blockage during inhalation without the irritation and discomfort normally associated with nasal dilators that are inserted within the nasal passages. By effectively relieving nasal blockage, the nasal dilator can reduce snoring sometimes associated with nasal blockage conditions. Moreover, this nasal dilator can be reliably worn at night when the inhalation nasal blockage problem is most acute, without the anxiety and inconvenience normally associated with custom made, internally worn nasal dilators or multi-element nasal dilators. In addition, the nasal dilator can be comfortably worn through extended therapeutic periods.

BRIEF DESCRIPTION OF THE DRAWINGS

FIG. 2 is an exploded perspective view showing the components of the nasal dilator in accordance with the present invention.

DETAILED DESCRIPTION OF THE PREFERRED EMBODIMENTS

Figure 1:
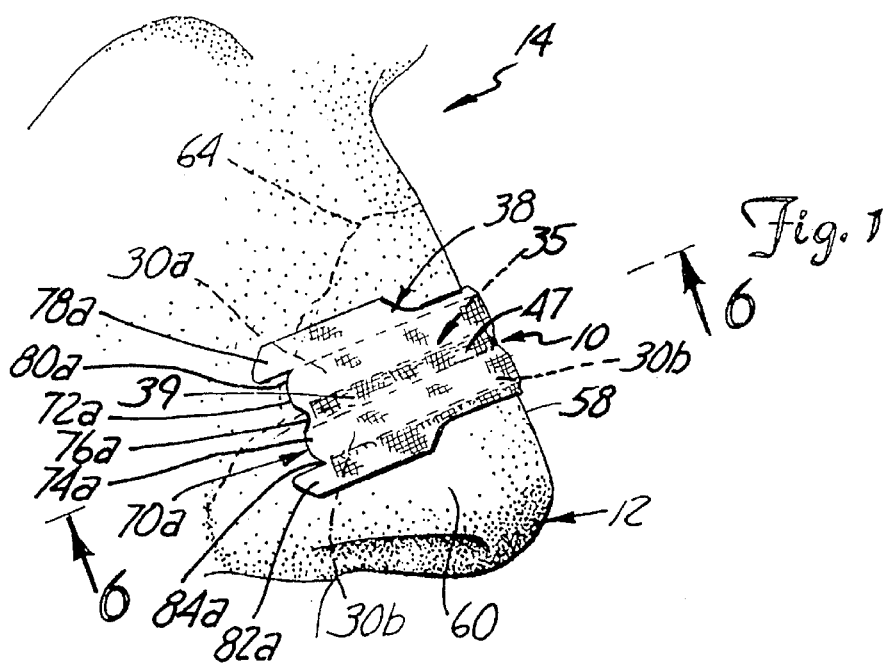
FIG. 1 is perspective view of a portion of a face with a nasal dilator in accordance with the present invention secured to a nose.

A nasal dilator 10 in accordance with the present invention is illustrated generally in FIG. 1. The nasal dilator 10 is shown secured to a nose 12 of a wearer 14.

As seen in FIG. 2, the nasal dilator 10 comprises a unitary truss member 16 including a flexible strip of base material 18 having a first end region 20 and a second end region 22 coupled to the first end region 20 by way of an intermediate segment 24. The width of the intermediate segment 24 is less than the width of the first and second end regions 20 and 22. The flexible strip of base material 18 is preferably formed of a polyester fabric that allows the skin of the nose 12 to breathe to maximize comfort and minimize irritation. A suitable, nonwoven, spunlaced, 100% polyester, fabric from which to form the base material 18 is available from E. I. DuPont Nemours & Co. (Old Hickory, Tenn.) under the tradename SONTARA®. SONTARA®, typically has a breaking strength property on a ratio of approximately 2:1 as determined by the machine direction (MD) (i.e., warp) relative to the cross direction (XD) (i.e., filling) of the fabric. In addition, SONTARA®, typically has an elongation percentage ratio of approximately 3:1 as determined by XD/MD of the fabric. The MD of the fabric is parallel to the longitudinal extent of the strip of base material 18.

The unitary truss member 16 further includes resilient means 26 secured to a first side 28 of the strip of base material 18, The resilient means 26 includes a first resilient hand 30a and a second resilient band 30b. The first resilient band 30a has a first end 41a and a second end 42a. The second resilient hand 30b has a first end 41b and a second end 42b. The first and second resilient hands 30a and 30b are each formed of a plastic material. For example, an industrial grade, biaxially oriented polyester that is approximately 0.080" to 0.135" wide and 0.010" thick. The relatively slight thickness of the material of each of the first and second resilient bands 30a and 30b enhances the axial, torsional flexibility of each of the first and second resilient bands 30a and 30b about the longitudinal extent of each of the bands 30a and 30b.

The first and second resilient bands 30a and 30b are secured by first and second, flexible strips of interface adhesive material 31a and 31b, to the first side 28 of the strip of base material 18. The first strip of interface adhesive material 31a has a first end 33a and a second end 34a. The second strip of interface adhesive material 31b has a first end 33b and a second end 34b. The first and second strips of interface adhesive material 31a and 31b are of the same size and shape as the first and second resilient bands 30a and 30b, respectively. The first resilient band 30a is secured, via the strip of adhesive material 31a, to the strip of base material 18 adjacent a first edge 32 of the intermediate segment 24. The second resilient band 30b is spaced from the first resilient band 30a, and is secured, via the strip of adhesive material 31b, to the strip of base material 18 adjacent a second edge 36 of the intermediate segment 24. The first and second resilient bands 30a and 30b are oriented generally parallel to one another and substantially parallel to the longitudinal extent of the flexible strip of base material 18. Each of the flexible strips of interface adhesive material 31a and 31b is preferably an acrylic, pressure sensitive bio-compatible adhesive material, such as (3M 1509) available from Minnesota, Mining & Manufacturing, Inc. (St. Paul, Minn.).

The unitary truss member 16 further includes a flexible strip of top material 38 having a first end region 39, a second end region 40 and an intermediate segment 47, that are of the same size and shape as the first end region 20, second end region 22 and intermediate segment 24, respectively, of the strip of base material 18. A bottom surface 35 of the strip of top material 38 includes a layer of an adhesive substance 48 that extends over the first and second end regions 39 and 40 and the intermediate segment 47. The adhesive substance 48 is a breathable, acrylic, pressure sensitive bio-compatible adhesive. The strip of top material 38 covers the first and second resilient bands 30a and 30b, and is secured to the first side 28 of the strip of base material 18 and to the resilient bands 30a and 30b by way of the layer of adhesive substance 48.

The strip of top material 38 helps to prevent the first and second resilient bands 30a and 30b from readily separating from the strip of material 18 and the strips of interface adhesive material 31a and 31b when the unitary truss member 16 is flexed. In addition, the strip of top material 38 stabilizes the strip of base material 18 by slightly stiffening the strip of base material 18 in its major plane, making the nasal dilator easier to put on and take off. The flexible strip of top material 38 is preferably a breathable, nonwoven material, such as (3M 1533) available from Minnesota, Mining & Manufacturing, Inc. (St. Paul, Minn.).

As seen in FIG. 2, a second side 44 of the strip of base material 18 includes a layer of an adhesive substance 46 that extends over the first and second end regions 20 and 22 and the intermediate segment 24. The adhesive substance 46 is a breathable, acrylic, pressure sensitive bio-compatible adhesive. Readily removable, first and second release liners 49 and 50, respectively, cover the adhesive substance 46 on the first and second end regions 20 and 22, respectively, of the strip of base material 18. Extensions 51 and 52 of the first and second release liners 49 and 50, respectively, cover the adhesive substance 46 on the intermediate segment 24 of the strip of base material 18. The first and second release liners 49 and 50 cover the adhesive substance 46 and remain in place on the strip of base material 18 until the nasal dilator 10 is to be used.

Figure 3:
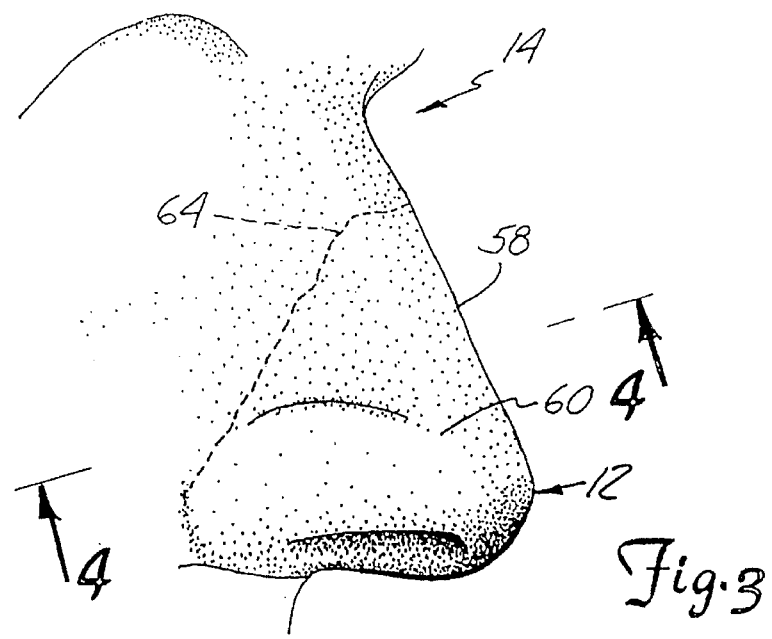
FIG. 3 is a perspective view similar to FIG. 1 with the nasal dilator in accordance with the present invention removed from the nose.
Figure 4:
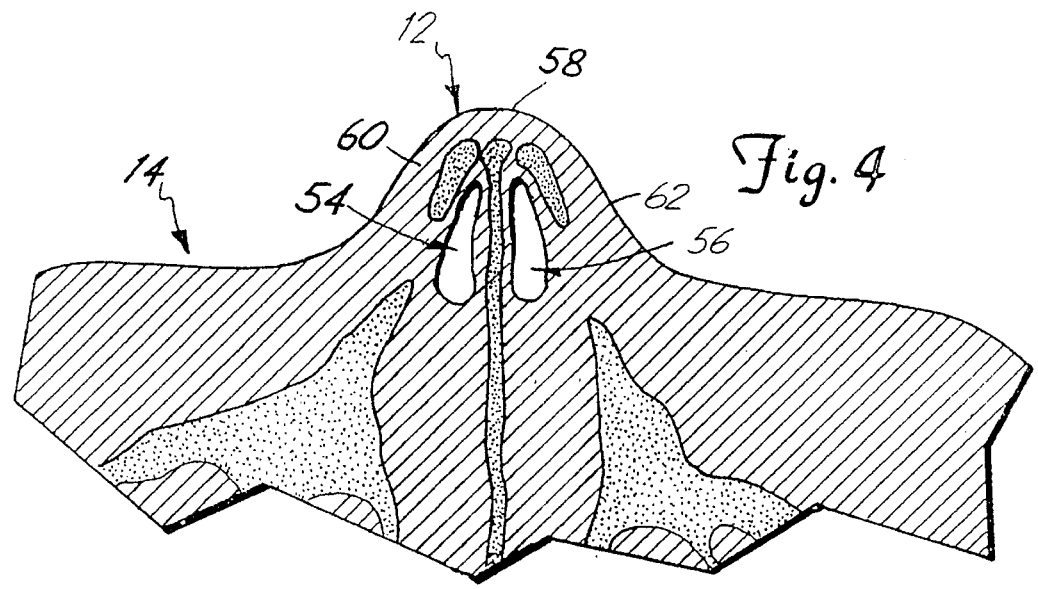
FIG. 4 is a sectional view taken along line 44 in FIG. 3 showing the nose in a state wherein no appreciable flow of air is occurring in the nasal passages.
Figure 5:
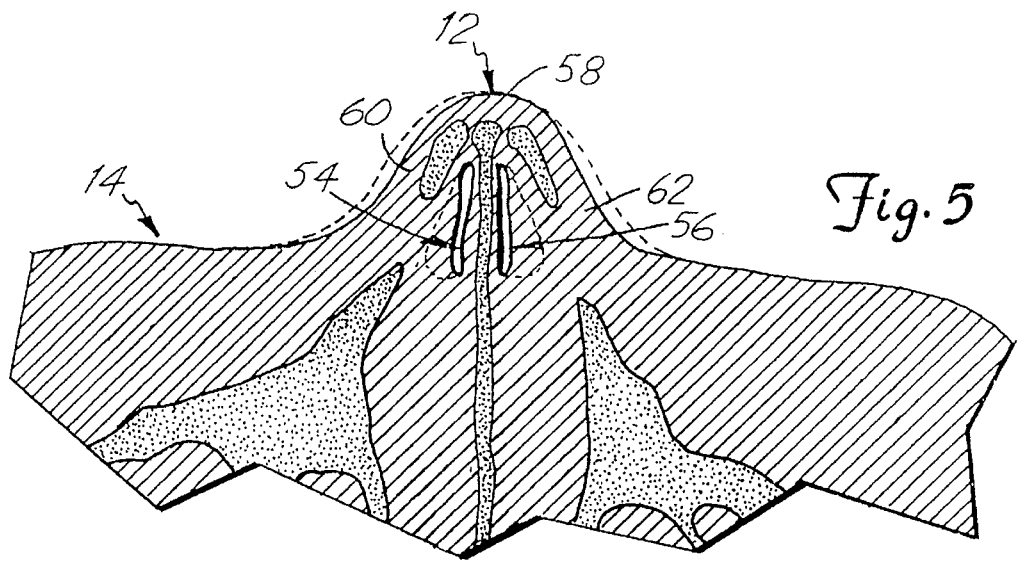
FIG. 5 is a sectional view similar to FIG. 4 showing the state of the nose during inhalation.

As seen in FIGS. 3 and 4, the nose 12 includes a first nasal passage 54, a second nasal passages 56 and a portion of the nose 12 known as the bridge 58 located between the first and second nasal passages 54 and 56. FIG. 4 shows the state of the first and second nasal passages 54 and 56 when no appreciable flow of air is occurring through the nasal passages 54 and 56. Due to a malformation, such as a deviated septum or swelling due to allergic reactions, outer wall tissue 60 and 62 of the first and second nasal passages 54 and 56, respectively, tends to be drawn in (i.e., collapse) during inhalation (see FIG. 5). This drawing in during inhalation is caused by reduced air pressure within the first and second nasal passages 54 and 56 as a result of an increase in air velocity as the in drawn breath travels through the narrowing of the nasal valves within the first and second nasal passages 54 and 56. The portion of the outer wall tissue 60 and 62 drawn in during inhalation is that located between the nasal bone 64 (shown in dashed lines in FIGS. 1 and 3) and the entrance to the nasal passages 54 and 56. This drawing in of the outer wall tissue 60 and 62 causes nasal blockage. The severity of the nasal blockage condition depends upon the how narrow the nasal valve is at the outset. The nasal dilator 10 of the present invention remedies this nasal blockage problem.

Figure 6:
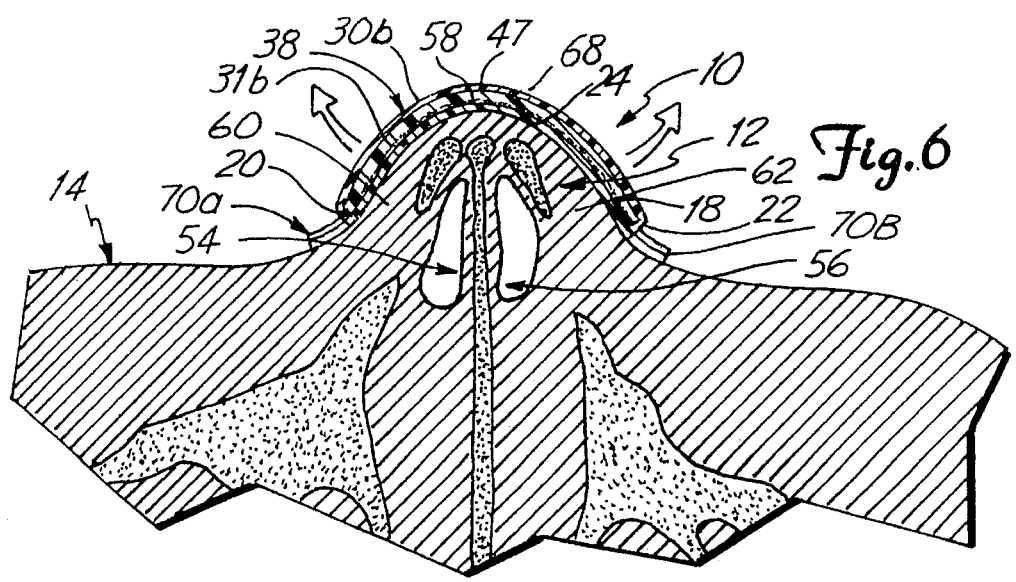
FIG. 6 is a sectional view taken along line 6—6 in FIG. 1 showing the state of the nose during inhalation with the nasal dilator in accordance with the present invention secured thereto.

To secure the nasal dilator 10 to the nose 12, the first and second release liners 49 and 50 are removed from the flexible strip of base material 18 to expose the adhesive substance 46. As seen in FIGS. 1 and 6, the nasal dilator 10 is placed on the exterior of the nose 12 such that the intermediate segment 24 traverses the bridge 58 of the nose 12 and the first and second end regions 20 and 22 contact the outer wall tissue 60 and 62 of the first and second nasal passages 54 and 56. The adhesive substance 46 on the first and second end regions 20 and 22 and the intermediate segment 24 releasably secures the unitary truss member 16 to the outer wall tissue 60 and 62 of the first and second nasal passages 54 and 56 and to the bridge 58 of the nose 12.

With the nasal dilator 10 in place about the nose 12, the resiliency of the first and second resilient bands 30a and 30b (i.e., the tendency of the resilient bands to return to their normally planar state shown in FIG. 2) acts to stabilize the outer wall tissue 60 and 62 and thereby prevents the outer wall tissue 60 and 62 of the first and second nasal passages 54 and 56 from drawing in during breathing (i.e., during inhalation). Moreover, the flexibility of the base material 18, strips of interface adhesive material 31a and 31b and top material 38, the resiliency of the first and second bands 30a and 30b, and the flexibility of the first and second resilient bands 30a and 30b due to the relatively slight thickness of the material of the bands 30a and 30b, all allow the nasal dilator 10 to closely conform to the curves of the nose of each individual wearer. The relatively slight thickness of the material of the bands 30a and 30b also enhances axial, torsional flexibility of the truss member 16 about the longitudinal extent of the truss member 16, which increases wearer comfort and facilitates adhesion of the adhesive substance 46.

In addition, the spunlaced fabric structure of the strip of base material 18, permits limited, primarily plastic and somewhat elastic deformation within the thickness of the base material 18. This limited, primarily plastic and somewhat elastic deformation property spreads out delaminating forces such as may be caused by: (1) the inherent tendency of the resilient bands to return to their normally planar state; (2) surface configuration differences between resilient bands 30a, 30b and the nose 12 of the wearer 14; and (3) displacement of the unitary truss member 16 relative to the outer wall tissue 60 and 62 as a result shear, tensile, cleavage and/or peel forces imparted at or to the outer wall tissue 60 and 62 and/or truss member 16 via wearer movement (e.g., nose gestures) and/or contact with an object (e.g., pillow); that may tend to cause the nasal dilator 10 to be inadvertently detached from the nose 12 of the wearer 14. By spreading out these delaminating forces, the strip of base material 18 acts as a buffering agent to prevent the transfer of focused forces to the adhesive substance 46 and thereby to the skin of the nose 12. Preventing the transfer of focused delaminating forces substantially eliminates any itching sensation (caused by the separation of the adhesive substance 46 from the skin) that a wearer 14 may have experienced if these delaminating forces were otherwise imparted to the skin of the nose 12.

A desired functional range of dilating force (i.e., the spring biasing force due to the resiliency of the resilient means of the nasal dilator) is typically in the range of 5 to 50 grams. Under 10 grams of dilating force is insufficient to help most wearers with any significant degree of nasal blockage upon inhalation. However, if the nasal blockage is mild enough, a positive effect may be noticed by the wearer with a little as 5 grams of dilating force provided by the dilator. A dilating force in excess of 40 grams may be somewhat obtrusive and uncomfortable for some dilator wearers.

The nasal dilator 10, of the present invention, is constructed to produce from 20 to 30 grams of dilating spring biasing force for each nasal outer wall 60 and 62. Each resilient band 30a and 30b is a portion of this total. Since two resilient bands 30a and 30b are used in the unitary truss member 16, and the resilient bands 30a and 30b are of equal proportions, each band 30a and 30b provides one half of the total designed spring biasing force.

Figure 7:
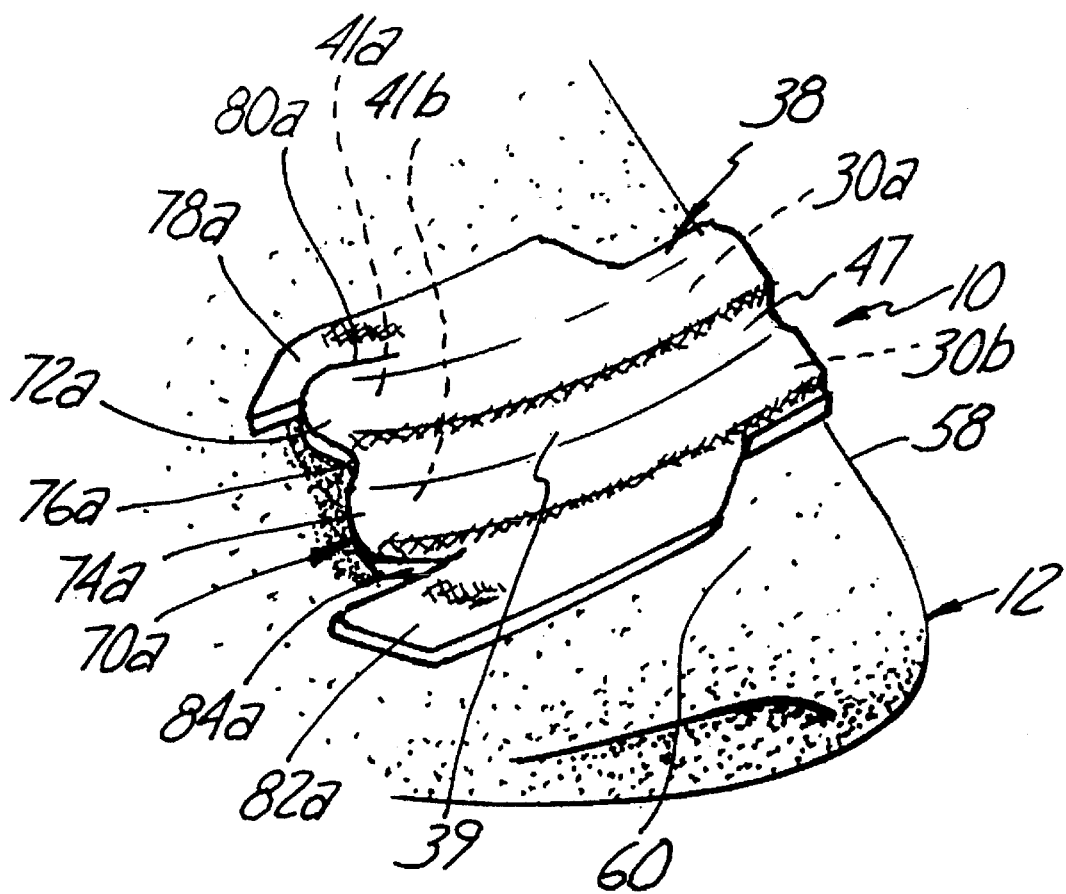
FIG. 7 is a greatly enlarged perspective view similar to FIG. 1 illustrating how the tip structure of the nasal dilator of the present invention prevents inadvertent peeling of the nasal dilator from the outer wall tissue of the nose.

As seen best in FIGS. 1 and 7, the unitary truss member 16, defined by the base material 18, strips of interface adhesive material 31a and 31b, top material 38 and resilient bands 30 and 30b, includes a first scalloped end edge 70a and a second scalloped end edge 70b. The first end edge 70a is defined by the first end regions 20 and 39 and first ends 41a, 41b, 33a and 33b. The second end edge 70b is defined by the second end regions 22 and 40 and second ends 42a, 42b, 34a and 34b. First and second end edges 70a and 70b are identical, so only the first end edge 70a will be described with particularity.

The first end edge 70a includes upper and lower protrusions 72a and 74a, respectively, separated by a valley 76a. The extent of the upper and lower protrusions 72a and 74a are defined by first ends 41a and 41b, respectively, of the resilient bands 30a and 30b, respectively; and the first ends 33a and 33b, respectively, of the strips of interface adhesive material 31a and 31b, respectively. Outboard and adjacent to the upper protrusion 72a is an upper extension 78a separated from the upper protrusion 72a by an upper back cut 80a. Outboard and adjacent to the lower protrusion 74a is a lower extension 82a separated from the lower protrusion 74a by a lower back cut 84a.

This nasal dilator tip structure, as defined by the end edges 70a and 70b, effectively minimizes any significant inadvertent peeling of the end regions 20 and 22 of the strip of base material 18 from the outer wall tissue 60 and 62 of the nasal passages 54 and 56 caused by the dilating, spring biasing force exerted by the resilient bands 30a and 30b, facial gestures and/or facial/nose contact with an object, such as a pillow. As can be seen in FIG. 7 in relation to end edge 70a, any inadvertent peeling (i.e., delamination of the end region 20 from the skin of the nose 12) caused by the bands 30a and 30b, facial gestures, etc. (which exert primarily peeling forces having some tensile force components at the ends 41a and 41b), will take place at the upper and lower protrusions 72a and 74a where the ends 41a and 41b of the resilient bands 30a and 30b are located, since the skin of the nose 12 is most likely to angle sharply away from the bands 30a and 30b at the edge of adhesion in the presence of the band forces. However, significant inadvertent peeling at the upper and lower protrusions 72a and 74a is greatly reduced by the upper and lower extensions 78a and 82a, which provide sufficient material extending beyond the ends 41a and 41b of the bands 30a and 30b and in adhesive contact with the skin of the nose 12 to suitably secure the end region 20 to the outer wall tissue 60 of the nose 12.

In addition, the discontinuity of shape of the materials at the intersection of the protrusions 72a,74a and the extensions 78a,82a, defined by the back cuts 80a,84a, redistribute and transform the peeling and tensile delaminating forces into primarily shear forces which are imparted to that material (i.e., the upper and lower extensions 78a and 82a) extending beyond shape discontinuity (i.e., back cuts 80a and 84a) further helps to minimize any significant inadvertent peeling of the end region 20. The redistribution and transformation of the peeling and tensile delaminating forces into primarily shear forces by the shape discontinuities (i.e., back cuts 80a and 84a) reduces inadvertent peeling, since under shear delaminating forces, adhesive, like adhesive substance 46 on the extensions 78a,82a and other portions of the end region 20, exhibits its stronger adhesion qualities when compared to the adhesion qualities under peeling delaminating forces.

Hence, any inadvertent delamination of the end region 20 from the skin of the nose 12 caused by the dilating, spring biasing force exerted by the resilient bands 30a and 30b, facial gestures, etc. is significantly minimized by the extension of material, defined by the extensions 78a,82a, past the ends 41a,41b of the bands 30a, 30b; and by the back cuts 80a and 84a which transform and redistribute the delaminating forces to the extensions 78a and 82a and the rest of the end region 20. Any slight inadvertent peeling of the end region 20 at the upper and lower protrusions 72a and 74a has the advantage that this peeled portion can be conveniently grasped by the wearer 14 for removing the nasal dilator 10 when desired. When desired, the nasal dilator 10 can be readily, manually removed by peeling the truss member 16 from the skin of the nose 12, such as by starting at the first end region 20 and progressing over the bridge 58 of the nose 12, until the second end region 22 is also free of the nose 12.

The nasal dilator 10 can be efficiently produced by a continuous manufacturing process, since the first and second ends 41a,b and 42a,b, respectively, of the first and second resilient bands 30a and 30b end at the first and second end edges 70a and 70b of the unitary truss member 16, unlike prior designs which require precutting of the resilient bands and centering of the bands on the base material. In the continuous manufacturing process, first and second continuous strips of interface adhesive material (31a and 31b) are first laminated to first and second continuous lengths of resilient band (30a and 30b) material, respectively. Next, a continuous sheet of base material (18) is laminated to the continuous strips of interface adhesive material (31a and 31b), and then a continuous sheet of top material (38) is laminated to the continuous sheet of base material (18) over the resilient band (30a and 30b) material. This unitary, laminated arrangement is then run through a die cutting station which cuts the laminated arrangement into unitary truss members 16. Because the resilient bands 30a and 30b extend to the end edges 70a and 70b, and are die cut with the laminated arrangement after the laminated arrangement is formed, the bands 30a and 30b are accurately positioned and aligned relative to the strip of base material 18 to provide a nasal dilator 10 that effectively dilates the nasal passages 54 and 56 to provide free breathing to the nasal dilator wearer 14.

This nasal dilator 10 is an efficient design that can be efficiently manufactured. The nasal dilator effectively prevents the outer wall tissue 60 and 62 of the first and second nasal passages 54 and 56 of the nose 12 from drawing in during breathing. In addition, the nasal dilator 10 provides effective relief of nasal blockage during inhalation without the irritation and discomfort normally associated with nasal dilators that are inserted within the nasal passages. By effectively relieving nasal blockage, the nasal dilator 10 can reduce snoring sometimes associated with nasal blockage conditions. Moreover, this nasal dilator 10 can be worn reliably at night when the inhalation nasal blockage problem is most acute, without the anxiety and inconvenience normally associated with custom made, internally worn nasal dilators or multi-element nasal dilators. In addition, the nasal dilator 10 can be comfortably worn through extended therapeutic periods.

Although the present invention has been described with reference to preferred embodiments, workers skilled in the art will recognize that changes may be made in form and detail without departing from the spirit and scope of the invention.

What is claimed is:

1. A nasal dilator for preventing outer wall tissue of nasal passages of a nose from drawing in during breathing, comprising:

a truss member including:

a first end region adapted to engage the outer wall tissue of a first nasal passage;

a second end region adapted to engage the outer wall tissue of a second nasal passage;

an intermediate segment coupling the first end region to the second end region and configured to traverse a portion of a nose located between the first and second nasal passages; and a resilient member extending along the truss member and having end portions that terminate at least at sections of end edges of the first and second end regions, the resilient member for acting to stabilize those outer wall tissues so engaged and thereby prevent such outer wall tissues of the first and second nasal passages from drawing in during breathing.

2. The nasal dilator of claim 1 wherein the truss member includes:

a flexible strip of base material defining the first and second end regions and the intermediate segment, the resilient member secured to a first side of the flexible strip of base material.

3. The nasal dilator of claim 2, and further including:

an adhesive substance located on a second side of the flexible strip of base material at the first and second end regions and the intermediate segment thereof for releasably securing the truss member to the outer wall tissue of the first and second nasal passages.

4. The nasal dilator of claim 3, and further including:

first and second release liners covering the adhesive substance on the first and second end regions and the intermediate segment of the flexible strip of base material, the first and second release liners being readily removable from the flexible strip of base material to expose the adhesive substance and permit the truss member to be secured to the outer wall tissue of the first and second nasal passages.

5. The nasal dilator of claim 2 wherein the resilient member includes:

at least one resilient band oriented substantially parallel to a longitudinal extent of the flexible strip of base material, the resiliency of the at least one resilient band acting to prevent the outer wall tissue of the first and second nasal passages from drawing in during breathing.

6. The nasal dilator of claim 1, and further including:

means at the end edges of the first and second end regions for preventing inadvertent delamination of the strip of base material from the outer wall tissue of the first and second nasal passages caused by dilating forces imparted to the strip of base material by the resilient means.

7. The nasal dilator of claim 6 wherein the means for preventing delamination includes a discontinuity of shape between first and second portions of the end edges of the first and second end regions of the truss member.

8. The nasal dilator of claim 1 wherein the end edge of each of the first and second end regions has a section of protrusions of a first length and a section of extensions of a second length different from the first length.

9. The nasal dilator of claim 8 wherein the extensions are longer than the protrusions.

10. A nasal dilator for preventing outer wall tissue of nasal passages of a nose from drawing in during breathing, comprising:

a truss member including:

a first end region adapted to engage the outer wall tissues of a first nasal passage;

a second end region adapted to engage the outer wall tissue of a second nasal passage;

an intermediate segment coupling the first end region to the second end region and configured to traverse a portion of a nose located between the first and second nasal passages;

a flexible strip of base material extending over at least a portion of the first and second end regions and the intermediate segment; and resilient means extending along the truss member including a first resilient band secured to the flexible strip of base material adjacent a first edge thereof and a second resilient band secured to the flexible strip of base material adjacent a second edge thereof such that each have end portions that terminate at least at sections of said end edges of the first and second end regions with the second resilient band being spaced from and extending generally parallel to the first resilient band, the resilient means acting to stabilize the outer wall tissue and thereby prevent the outer wall tissue of the first and second nasal passages from drawing in during breathing.

11. The nasal dilator of claim 10 wherein the first and second resilient bands are secured to the first side of the flexible strip of base material via an interface adhesive material.

12. The nasal dilator of claim 11 and further including:

a strip of top material that covers the first and second resilient bands and is adhesively secured to the flexible strip of base material.

13. The nasal dilator of claim 10 wherein the end edges of the first and second end regions are shaped with radius corners to prevent inadvertent peeling of the strip of base material from the outer wall tissue of the first and second nasal passages caused by dilating forces imparted to the strip of base material by the resilient bands.

14. The nasal dilator of claim 13 wherein the end edges of each of the first and second end regions includes:

a pair of spaced, first and second protrusions that are defined by the first and second resilient bands, respectively; and a pair of spaced, first and second extensions, the first and second extensions being located outboard and extending past the first and second protrusions, respectively, to prevent inadvertent peeling of the strip of base material from the outer wall tissue of the first and second nasal passages.

15. The nasal dilator of claim 14 wherein respective first extensions and protrusions and respective second extensions and protrusions are separated by back cut portions in the truss member that distribute delaminating forces, caused by the first and second resilient bands, to the first and second end regions.

16. A nasal dilator for preventing outer wall tissue of nasal passages of a nose from drawing in during breathing, comprising:

a truss member including:

a first end region adapted to engage the outer wall tissue of a first nasal passage;

a second end region adapted to engage the outer wall tissue of a second nasal passage;

an intermediate segment coupling the first end region to the second end region and configured to traverse a portion of a nose located between the first and second nasal passages; and resilient means extending along the truss member and having end portions that terminate at least at sections of end edges of the first and second end regions, a back cut provided extending into said truss member at each of said end edges of the first and second end regions which is located between a portion of the resilient means and a further portion of the truss member at first and second end regions of the truss member for preventing inadvertent delamination of the strip of base material from the outer wall tissue of the first and second nasal passages.

17. A nasal dilator capable of introducing separating stresses in nasal outer wall tissues, comprising:

a truss having a pair of spaced apart end regions each having a side terminated by end edges at opposite ends of said truss such that if said spaced apart end region sides are forced toward one another from initial positions to substantially reduce said spacing therebetween by a spacing reduction force external to said truss, restoring forces result in said truss sufficient to restore a substantial fraction of said spacing between said end region sides absent such spacing reduction forces; and an engagement means adhered to said end region sides and capable of engaging exposed surfaces of such outer wall tissues sufficiently to remain so engaged against said restoring forces, said pair of end region sides with said engagement means adhered thereto each including as part thereof at least one corresponding extension with said extension being separated in part from at least some other portion of that said end region of which it is a part with said separation extending into that said end region from said end edge thereof.

18. The dilator of claim 17 wherein said extensions each extend past at least some other portion of that said end region of which it is a part, and so extends substantially parallel to a direction oriented through said opposite ends of said truss.

19. The dilator of claim 18 wherein there is another extension included in each said end region also extending past said other portion of that said end region, said other portion in a said corresponding end region being positioned between those said extensions therein to thereby form a primarily concave opening between said extensions.

20. The dilator of claim 17 wherein said truss has a resilient member therein having opposite ends each ending short of at least a portion of said end edges.

21. The dilator of claim 17 wherein said truss has a resilient member therein having opposite ends each reaching at least a portion of said end edges.

22. The dilator of claim 17 wherein said truss has a resilient member and a flexible strip therein with said resilient member positioned at least in part between said flexible strip and any said exposed surfaces of nasal outer wall tissue so engaged.

23. The dilator of claim 22 wherein said truss also includes a base flexible strip positioned at least in part between said resilient member and any exposed surface of nasal outer wall tissue to be so engaged.

24. The dilator of claim 17 wherein said dilator is configured to restrain nasal outer wall tissues adjacent nasal passages therein from being drawn in during breathing, said truss having sufficient restoring forces to substantially maintain during inhalation that spacing occurring between end surfaces prior to inhalation.

25. The dilator of claim 24 wherein said end surfaces are limited in separation therebetween so that, when said end surfaces are engaging nasal outer wall tissues adjacent nasal passages therein, a surface of said truss can be in contact with that nose containing said outer wall tissues for substantially all of that extent thereof between said end surfaces.

26. The dilator of claim 17 wherein said truss and said engagement means are capable of being manually released from exposed surfaces of any nasal outer wall tissues so engaged by said engagement means.

27. The dilator of claim 26 wherein said engagement means is an adhesive substance located on each of said pair of spaced-apart end surfaces and capable of adhering to exposed surfaces of nasal outer wall tissues while adhering to said truss and yet permitting said truss and said engagement means to be manually released from exposed surfaces of any nasal outer wall tissues adhered to by said engagement means.

28. The dilator of claim 17 wherein said truss and said engagement means together are formed as a strip having a length substantially greater than either of its width and thickness, and a width substantially greater than its thickness everywhere along said length.

29. The dilator of claim 28 wherein said strip is substantially planar absent external forces applied thereto.

30. The dilator of claim 17 wherein said restoring forces in said truss arising if said end surfaces are forced adjacent to one another by said spacing reduction forces are sufficient, upon removal of said spacing reduction forces, to restore most of said direct spacing present between said end surfaces before application of such spacing reduction forces.

31. A nasal dilator capable of introducing separating stresses in nasal outer wall tissues, comprising:

a truss of a single body having a pair of spaced apart end surfaces which, if forced toward one another from initial positions to substantially reduce direct spacing therebetween by spacing reduction force external to said truss, results in restoring forces in said truss tending to restore said direct spacing between said end surfaces; and engagement means adhered to said end surfaces and capable of engaging exposed surfaces of nasal outer wall tissue sufficiently to remain so engaged against said restoring forces, said truss having a resilient member and a flexible strip therein with said resilient member positioned at least in part between said flexible strip and any exposed surfaces of nasal outer wall tissues so engaged.

32. The dilator of claim 31 wherein said resilient member has opposite ends thereof each ending short of at least a portion of end edges at opposite ends of said truss.

33. The dilator of claim 31 wherein said resilient member has opposite ends thereof each reaching at least a portion of end edges at opposite ends of said truss.

34. The dilator of claim 31 wherein said dilator is configured to restrain nasal outer wall tissues adjacent nasal passages therein from being drawn in during breathing, said truss having sufficient restoring forces to substantially maintain during inhalation that spacing occurring between said end surfaces prior to inhalation.

35. The dilator of claim 34 wherein said end surfaces are limited in separation therebetween so that, when end surfaces are engaging nasal outer wall tissues adjacent nasal passages therein, a surface of said truss can be in contact with the nose for substantially all of that extent thereof between said end surfaces.

36. The dilator of claim 31 wherein said truss and said engagement means are capable of being manually released from exposed surfaces of any nasal outer wall tissues engaged by said engagement means.

37. The dilator of claim 36 wherein said engagement means is an adhesive substance located on each of said pair of spaced-apart end surfaces and capable of adhering to exposed surfaces of nasal outer wall tissues while adhering to said truss and yet permitting said truss and said engagement means to be manually released from exposed surfaces of any nasal outer wall tissues adhered to by said engagement means.

38. The dilator of claim 31 wherein said truss and said engagement means together are formed as a strip having a length substantially greater than either of its width and thickness, and a width substantially greater than its thickness everywhere along said length.

39. The dilator of claim 38 wherein said strip is substantially planar absent external forces applied thereto.

40. The dilator of claim 31 wherein said restoring forces in said truss arising if said end surfaces are forced adjacent to one another by said spacing reduction forces are sufficient, upon removal of said spacing reduction forces, to restore most of said direct spacing present between said end surfaces before application of such spacing reduction forces.

41. The dilator of claim 31 wherein said truss further includes a base flexible strip positioned between said resilient member and any exposed surfaces of nasal outer wall tissue so engaged.

* * * * *

UNITED STATES PATENT AND TRADEMARK OFFICE
CERTIFICATE OF CORRECTION

PATENT NO. : 5,533,503

DATED : JULY 9, 1996

INVENTOR(S) : WILLIAM J. DOUBEK, DANIEL E. COHEN, BRUCE C. JOHNSON

It is certified that error appears in the above-indentified patent and that said Letters Patent is hereby corrected as shown below:

Col. 4, line 47, delete "44", insert --4 - 4--

Col. 5, line 23, after "18", delete ",", insert --.--

Col. 5, line 26, after "resilient", delete "hand", insert --band--

Col. 5, line 27, after "resilient", delete "hands", insert --bands--

Col. 12, line 66, delete "that nose containing said outer wall tissues", insert --the nose--

Signed and Sealed this

Twenty-sixth Day of November 1996

Attest:

BRUCE LEHMAN

Attesting Officer      Commissioner of Patents and Trademarks

(12) EX PARTE REEXAMINATION CERTIFICATE (5615th)
United States Patent
Doubek et al.

(10) Number: US 5,533,503 C1
(45) Certificate Issued: Nov. 28, 2006

(54) NASAL DILATOR

(75) Inventors: William J. Doubek, Circle Pines, MN (US); Daniel E. Cohen, Eden Prairie, MN (US); Bruce C. Johnson, St. Paul, MN (US)

(73) Assignee: Creative Integration & Design, Inc., St. Paul, MN (US)

Reexamination Request:
No. 90/007,181, Aug. 23, 2004

Reexamination Certificate for:
Patent No.: 5,533,503
Issued: Jul. 9, 1996
Appl. No.: 08/314,547
Filed: Sep. 28, 1994

Certificate of Correction issued Nov. 26, 1996.

Related U.S. Application Data

(63) Continuation of application No. 08/050,554, filed on Apr. 20, 1993, now abandoned, and a continuation of application No. 08/048,589, filed on Apr. 16, 1993, now abandoned, which is a continuation of application No. 07/884,626, filed on May 15, 1992, now abandoned, which is a continuation of application No. 07/712,508, filed on Jun. 10, 1991, now abandoned, said application No. 08/050,554, filed on Apr. 20, 1993, now abandoned, is a continuation-in-part of application No. 08/048,589, filed on Apr. 16, 1993, now abandoned.

(51) Int. Cl.
*A61F 5/56* (2006.01)
*A62B 7/00* (2006.01)
A61F 5/08

(52) U.S. Cl. .......................... 128/200.24; 128/207.18; 128/848; 606/204.45; 602/902

(58) Field of Classification Search ...................... None
See application file for complete search history.

(56) References Cited

U.S. PATENT DOCUMENTS 2,633,128 A * 3/1953 Schaefer ...................... 602/42
RE35,408 E * 12/1996 Petruson ...................... 128/858

FOREIGN PATENT DOCUMENTS

ES                 289561       *   4/1986

* cited by examiner

*Primary Examiner*—Kenneth Bomberg

(57) ABSTRACT

A nasal dilator that prevents the outer wall tissue of the nasal passages of the nose from drawing in during breathing comprises a truss member. The truss member includes a flexible strip of material having a first end region, a second end region and intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing. An end edge tip structure of the first and second end regions prevents inadvertent peeling of the truss member from the outer wall tissue, caused by the resiliency of the first and second resilient bands.

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10–30 is confirmed.

Claims 1, 2, 3, 6, 8, 31 and 33 are determined to be patentable as amended.

Claims 4, 5, 7, 9, 32 and 34–41, dependent on an amended claim, are determined to be patentable.

1. A nasal dilator for preventing outer wall tissue of nasal passages of a nose from drawing in during breathing, comprising:
   a truss member including:
      a first end region adapted to engage the outer wall tissue of a first nasal passage;
      a second end region adapted to engage the outer wall tissue of a second nasal passage;
      an intermediate segment coupling the first end region to the second end region and configured to traverse a portion of a nose located between the first and second nasal passages; and
      a resilient member *coupled to a defining base, the defining base extending past at least one of two opposite sides of said resilient member at least at one location along those said sides, the resilient member* extending along the truss member and having end portions that terminate at least at sections of end edges of the first and second end regions, the resilient member for acting to stabilize those outer wall tissues so engaged and thereby prevent such outer wall tissues of the first and second nasal passages from drawing in during breathing.

2. The nasal dilator of claim 1 wherein the truss member includes:
   a flexible strip of base material *as said defining base for* defining the first and second end regions and the intermediate segment, the resilient member secured to a first side of the flexible strip of base material.

3. [The nasal dilator of claim 2, and further including:] *A nasal dilator for preventing outer wall tissue of nasal passages of a nose from drawing in during breathing, comprising:*
   *a truss member including:*
      *a first end region adapted to engage the outer wall tissue of a first nasal passage;*
      *a second end region adapted to engage the outer wall tissue of a second nasal passage;*
      *an intermediate segment coupling the first end region to the second end region and configured to traverse a portion of a nose located between the first and second nasal passages;*
      *a flexible strip of base material defining the first and second end regions and the intermediate segment;*
      *a resilient member extending along the truss member and having end portions that terminate at least at sections of end edges of the first and second end regions, the resilient member secured to a first side of the flexible strip of base material for acting to stabilize those outer wall tissues so engaged and thereby prevent such outer wall tissues of the first and second nasal passages from drawing in during breathing; and*
   an adhesive substance located on a second side of the flexible strip of base material at the first and second end regions and the intermediate segment thereof for releasably securing the truss member to the outer wall tissue of the first and second nasal passages.

6. [The nasal dilator of claim 1, and further including:] *A nasal dilator for preventing outer wall tissue of nasal passages of a nose from drawing in during breathing, comprising:*
   *a truss member including:*
      *a first end region adapted to engage the outer wall tissue of a first nasal passage;*
      *a second end region adapted to engage the outer wall tissue of a second nasal passage;*
      *an intermediate segment coupling the first end region to the second end region and configured to traverse a portion of a nose located between the first and second nasal passages;*
      *a flexible strip of base material defining the first and second end regions and the intermediate segment;*
      *a resilient member extending along the truss member and having end portions that terminate at least at sections of end edges of the first and second end regions, the resilient member for acting to stabilize those outer wall tissues so engaged and thereby prevent such outer wall tissues of the first and second nasal passages from drawing in during breathing; and*
   means at the end of the first and second end regions for preventing inadvertent delamination of the strip of base material from the outer wall tissue of the first and second nasal passages caused by dilating forces imparted to the strip of base material by the resilient means.

8. [The nasal dilator of claim 1 wherein] *A nasal dilator for preventing outer wall tissue of nasal passages of a nose from drawing in during breathing, comprising:*
   *a truss member including:*
      *a first end region adapted to engage the outer wall tissue of a first nasal passage;*
      *a second end region adapted to engage the outer wall tissue of a second nasal passage;*
      *an intermediate segment coupling the first end region to the second end region and configured to traverse a portion of a nose located between the first and second nasal passages;*
      *a resilient member extending along the truss member and having end portions that terminate at least at sections of end edges of the first and second end regions with* the end edge of each of the first and second end regions [has] *having* a section of protrusions of a first length and a section of extensions of a second length different from the first length, *the resilient member for acting to stabilize those outer wall tissues so engaged and thereby prevent such outer wall tissues of the first and second nasal passages from drawing in during breathing.*

31. A nasal dilator capable of introducing separating stresses in nasal outer wall tissues, comprising:

a truss of a single body having a pair of spaced apart end surfaces which, if forced toward one another from initial positions to substantially reduce direct spacing therebetween by spacing reduction force external to said truss, results in restoring forces in said truss tending to restore said direct spacing between said end surfaces; and engagement means adhered to said end surfaces and capable of engaging exposed surfaces of nasal outer wall tissue sufficiently to remain so engaged against said restoring forces, said truss having a resilient member and a flexible strip therein with said resilient member positioned at least in part between said flexible strip and any exposed surfaces of nasal outer wall tissues so engaged, *said resilient member having an adherence surface and with an adhesive on that adherence surface thereof, said adherence surface facing directions at least in part that are faced by said end surfaces.*

33. [The dilator of claim 31 wherein] *A nasal dilator capable of introducing separating stresses in nasal outer wall tissues, comprising:*

*a truss of a single body having a pair of spaced apart end surfaces which, if forced toward one another from initial positions to substantially reduce direct spacing therebetween by spacing reduction force external to said truss, results in restoring forces in said truss tending to restore said direct spacing between said end surfaces; and*

*engagement means adhered to said end surfaces and capable of engaging exposed surfaces of nasal outer wall tissue sufficiently to remain so engaged against said restoring forces, said truss having a resilient member and a flexible strip therein with said resilient member positioned at least in part between said flexible strip and any exposed surfaces of nasal outer wall tissues so engaged,* said resilient member [has] *having* opposite ends thereof each reaching at least a portion of end edges at opposite ends of said truss.

* * * * *